United States Patent [19]

Hertel et al.

[11] Patent Number: 5,097,574
[45] Date of Patent: Mar. 24, 1992

[54] METHOD AND APPARATUS FOR FORMING FLUFF PADS FOR DIAPERS AND THE LIKE

[75] Inventors: James E. Hertel; John R. Merkatoris; Grantland A. Craig, all of Green Bay, Wis.

[73] Assignee: Paper Coverting Machine Company, Green Bay, Wis.

[21] Appl. No.: 620,627

[22] Filed: Dec. 3, 1990

Related U.S. Application Data

[63] Continuation-in-part of Ser. No. 514,199, Apr. 25, 1990, Pat. No. 5,044,052.

[51] Int. Cl.⁵ .................. D04H 1/04; D01G 23/08
[52] U.S. Cl. ........................... 28/105; 19/308; 264/121
[58] Field of Search .......... 28/104, 105, 106, 116–130, 28/140, 158; 26/18.6; 19/56, 145.7, 148, 301, 304, 308; 264/121, 304, 517; 425/80.1, 81.1; 604/358

[56] References Cited

U.S. PATENT DOCUMENTS

| | | | |
|---|---|---|---|
| 3,483,051 | 12/1969 | Mesek et al. | 19/308 X |
| 3,857,657 | 12/1974 | Teed | 19/301 X |
| 3,862,867 | 1/1975 | Marshall | 264/121 X |
| 3,939,240 | 2/1976 | Savich | 28/121 X |
| 3,963,392 | 6/1976 | Goyal | 19/145.5 |
| 3,981,708 | 9/1976 | Loeffler et al. | 264/112 |
| 3,984,898 | 10/1976 | Matsumura et al. | 19/156.3 |
| 4,153,977 | 5/1979 | Moser | 19/308 X |
| 4,264,290 | 4/1981 | Dunkerly, II et al. | 264/121 X |
| 4,598,441 | 7/1986 | Stemmler | 19/148 X |
| 4,666,647 | 5/1987 | Enloe et al. | 19/148 X |
| 4,674,966 | 6/1987 | Johnson et al. | 19/148 X |
| 4,859,388 | 8/1989 | Peterson et al. | 264/121 |
| 4,908,175 | 3/1990 | Angstadt | 264/121 X |
| 5,004,579 | 4/1991 | Wislinski et al. | 264/517 |

*Primary Examiner*—Werner H. Schroeder
*Assistant Examiner*—Amy Brooke Vanatta
*Attorney, Agent, or Firm*—Tilton, Fallon, Lungmus & Chestnut

[57] ABSTRACT

A method and apparatus for forming fluff pads and the like wherein fluff providing material webs are introduced into separate hammermills and then delivered through a plurality of ducts through a moving screen under vacuum and wherein the ducts are characterized by reverse bends to densify the particle stream at the outside of the curvature for generally perpendicular deposition on the screen.

1 Claim, 2 Drawing Sheets

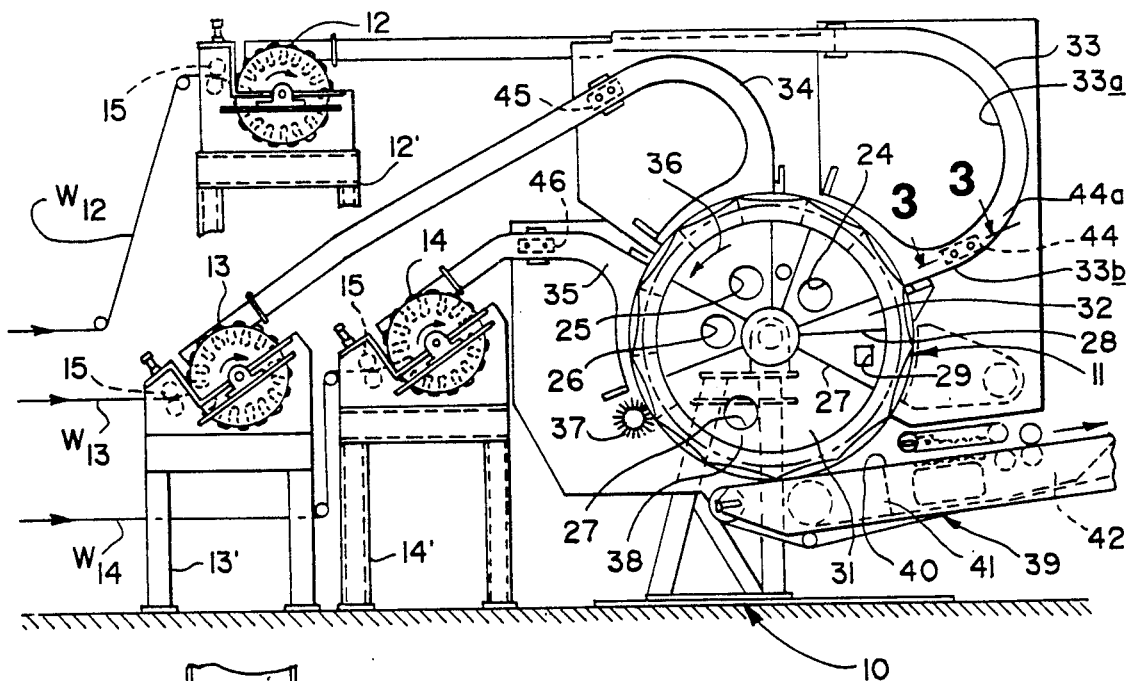
Fig. 1
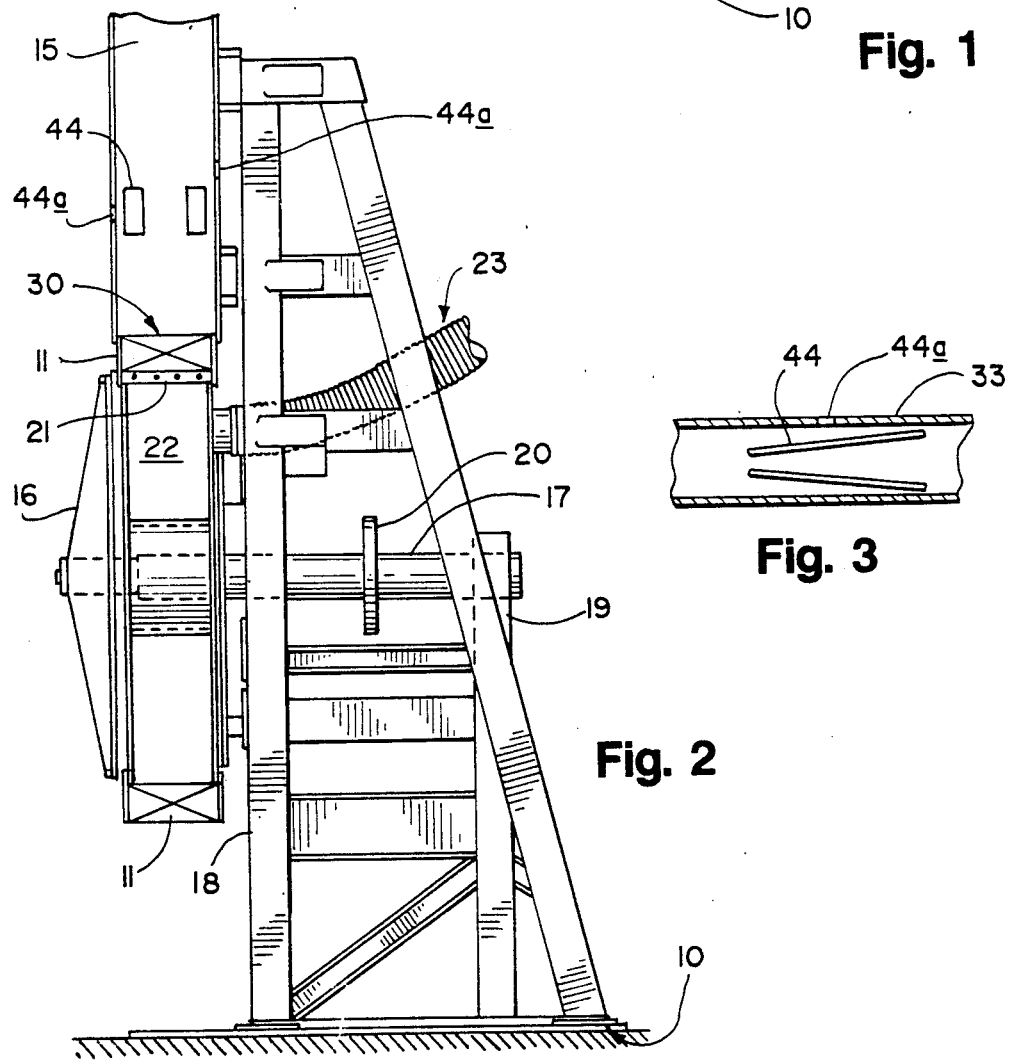
Fig. 2
Fig. 3

METHOD AND APPARATUS FOR FORMING FLUFF PADS FOR DIAPERS AND THE LIKE

This is a continuation-in-part of our co-pending application Ser. No. 514,199 filed Apr. 25, 1990, now U.S. Pat. No. 5,044,052.

BACKGROUND AND SUMMARY OF THE INVENTION

This invention relates to a method and apparatus for forming fluff pads for diapers and the like, and more particularly, to apparatus employing a moving screen—as on a rotating drum and novel ductwork. Fluff forming screens have been known for a considerable time—see, for example, co-owned Pat. No. 3,599,293. This invention provides novel means for depositing the fluff particles on the screen.

Typical fluff forming systems, both drum and wire, use large "boxes" positioned over forming wires. These boxes, or forming hoods, are supplied with a fiber/air mixture (typically 0.005 to 0.03 lb. fiber cubic foot of air) which is then drawn toward the screen through air flow and gravity forces.

Problems often encountered in these basic forming methods are:
uneven fiber density in the pad;
"clumping" due to air turbulence; i.e., formation of "fiber balls" prior to laydown;
clumping due to rolling or picking of the pad by high velocity air tangent to the screen; i.e., air scrubbing off part of the pad and redepositing it as a clump;

To obtain a high pad integrity it is necessary to have a high air flow through the pad during forming. However, the large volume of the forming box allows air turbulence and instability and, hence, the clumping problems described above. These instabilities are usually seen as eddies or pulsing in the forming box.

One method (U. S. Pat. No. 4,494,278) for reducing or eliminating these problems was to mill the fluff and air convey it to the forming hood with general disregard for clumping. Then, the fiber/air mixture was introduced into an agitated box over the forming wire. The fibers were then redistributed and sifted through a screen before falling onto the wire to form the pad.

In other formers, fibers are conveyed to hoppers which feed secondary milling rotors immediately above the forming area. This and the '278 method both overcome the problems listed but require significantly more equipment than the simple forming box.

In one aspect the invention includes a frame providing a longitudinally extending path, a drum mounted on the frame having a circumferentially extending screen, means for rotating the drum in one direction, a vacuum source associated with the frame for maintaining a vacuum inside the drum, fluff mill means in the path on one side of the drum to provide (with the vacuum source) a fluff particle stream, a take-away conveyor in the path on the other side of the drum, a plurality of longitudinally extending fluff delivery ducts on the frame in the path each having a first end connected to the mill means and a second end communicating with the screen, the duct second end including a reverse bend section elongated in the direction of drum rotation whereby the outer side of side reverse bend intensifies the fluff particle steam thereagainst to achieve fluff particle deposit on the screen without substantial turbulence.

In another patent (No. 4,904,440) dealing with pad formation, the output of the hammermill is split into a plurality of streams for vacuum-induced delivery to a drum. In another aspect of this invention, we split the material input to separate hammermill means and this results in several benefits over a single mill with a splitting device at the outlet.
1. Allows independent control of airflow and vacuum for each forming chamber without affecting the fluff separation ratios.
2. Prevents mixing so that a different fluff material can be accurately layered into the forming pad.
3. Trim pieces (i.e., from the pad leg cutouts) can be introduced into a single mill chamber and hence directed to a specific layer in the pad.
4. Allows use of long length fluff fibers (i.e., synthetic fibers) without the problems associated with buildup on the leading edges of the splitting devices.

BRIEF DESCRIPTION OF DRAWING:

The invention is described in conjunction with an illustrative embodiment in the accompanying drawing, in which:

FIG. 1 is a side elevational view of apparatus employed in the practice of the invention;

FIG. 2 is an end elevational view of the apparatus of FIG. 1;

FIG. 3 is an enlarged sectional view taken along the line 3—3 of FIG. 1;

DETAILED DESCRIPTION

Figure 4:
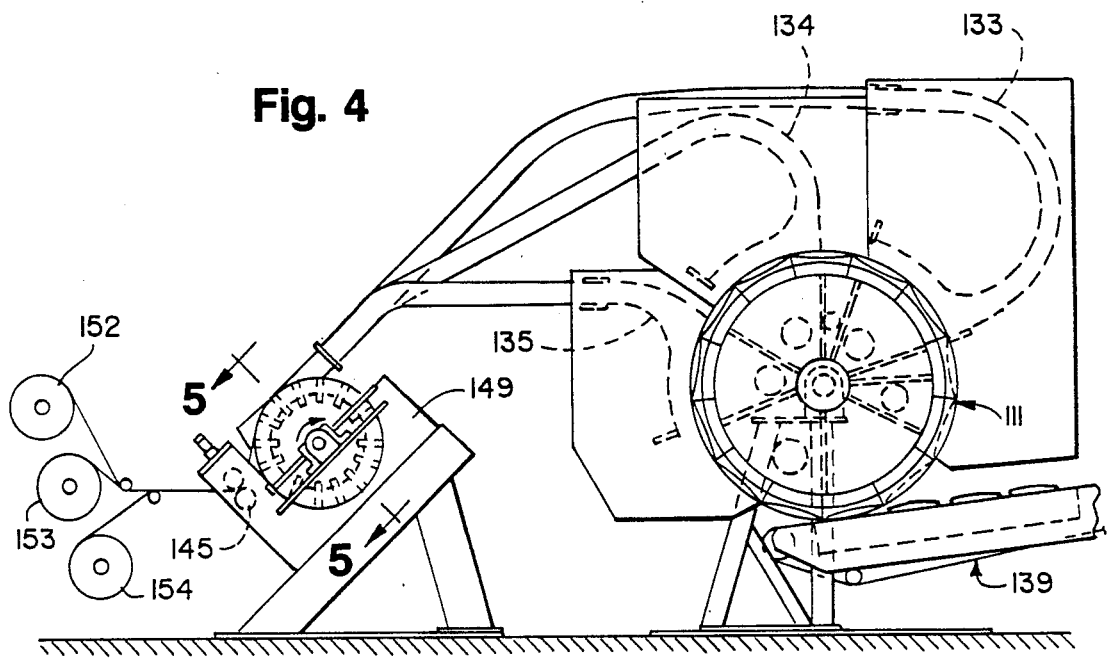
FIG. 4 is a view similar to FIG. 1 but of a modified form of apparatus.

Referring first to FIG. 1, the numeral 10 designates generally a frame for rotatably supporting an annular drum generally designated 11 and which is operably associated with hammermills 12, 13 and 14 suitably supported on frames 12', 13' and 14'. Each mill 12-14 is fed by its own web as at $W_{12}$, $W_{13}$ and $W_{14}$ via pull rolls 15 on each frame 12'-14'. The pulp webs are converted to fluff fibers and delivered via ducts (to be described hereinafter) to the drum 11.

More particularly, the annular drum 11 includes a spider 16 (see the left hand portion of FIG. 2) which is supported by a drive shaft 17 carried in ball bearing pillow blocks as at 18 and 19—all being part of the frame 10. A drive is indicated schematically at 20 in the form of a sheave operably associated with a drive motor and belt (not shown).

Still referring to FIG. 2 the inner wall of the annular drum 11 as at 21 is sealingly related to a plenum 22, portions of which are exhausted by a vacuum connection generally designated 23. Only one such connection is shown in FIG. 2 but in the illustrated embodiment as seen in FIG. 1, we provide four vacuum ports as at 24, 25, 26 and 27. Radial vanes are provided at a plurality of angularly related positions, a first of which is designated 27. The vane 27 in the stationary plenum 22 along with a second vane 28 defines a chamber for introducing air through the inlet port 29 which is used for cleaning the screen. The screen provided in the annular drum is schematically represented at 30 in FIG. 2. Chambers as at 31 and 32 (now referring to FIG. 1) and which flank the chamber with the air inlet opening 29 are unused, being neither under pressure nor vacuum.

Streams of fluff particles are introduced through the ducts 33, 34 and 35 which are relatively elongated at their outlet ends in the direction of screen movement, i.e., rotation of the annular drum 11 as indicated by the arrow in the central part of FIG. 1 and which is designated 36.

After the fluff has been deposited on the screen 30 of the annular drum 11 from the three ducts 33—35, the now-formed fluff pads pass by a scarfing wheel 37 rotatably mounted on the frame in conventional fashion.

We provide a baffle for the vacuum as at 38 to reduce the holding force on the pads so that the pads can be stripped by a takeaway conveyor 39 movably mounted on the frame 10. The takeaway conveyor 39 includes an endless belt 40 which advantageously is foraminous or otherwise air permeable to allow vacuum to draw the pads from the drum 11. A first vacuum chamber is provided as at 41 and a second vacuum chamber as at 42 as part of the takeaway conveyor.

We have found the structure of the fluff-supply ducts to be especially advantageous in achieving the benefits of the invention. More particularly, in order to stabilize the air mass in the forming section, the fiber/air mixture is separated into multiple ducts in route to the pad former. This allows smaller cross-sections and avoids unstable air behaviors.

Prior to fiber laydown the duct curvature causes the fiber/air mixture to stratify; i.e., the fiber density is higher than air and thus the fiber concentration at the outside of the curve is greater than than at the inside of the curve. The high concentration portion of the flow is directed at a small angle from normal (approximately perpendicular) to the forming wire (pad form) and at high velocity without turbulent mixing. The lower concentration portion (inside track) is slowed down by an expansion of the duct area. Design parameters for the duct shapes can be generally described as:

cross sectional areas are set to maintain flow velocities in the range of 40 to 200 feet per second;
changes in direction are gradual; i.e., radii of curvature are typically greater than four times the duct height;
high concentration flow area (outside of duct curve) is directed roughly normal to the forming surface;
final shape of the "inside" curve follows natural expansion of air flow stream into chamber;

In addition to the improved air flow stability, the invention also offers the benefits of;

space between separate forming sections, i.e., duct outlets, for introduction of superabsorbent powder into a specific layer of the pad;
potential to make multi layer pads of dissimilar fluff materials;
ability to tailor forming air flows for start of pad formation (high volume/low pressure) separate from end of pad formation (low volume/high pressure).

Duct Construction

We have found it particularly advantageous to construct the delivery duct work in two different cross sectional areas adjacent the discharge end—as can be readily appreciated from a consideration of FIG. 1. There each duct 33—35 is seen to include a reverse bend or general C-shape with the bottom of the C-shape being relatively elongated and open to the screen 30 on the drum 11. More particularly the inner side of each duct as at 33a (relative to the duct 33) is generally C-shaped whereas the outer side as at 33b is only partially C-shaped to provide the discharge end of the duct work with an opening as at 43 facing the screen. As mentioned previously the outer side 33b of the reverse bend section achieves a densification of the particle stream adjacent to itself so as to develop a deposition of the fluff particles on the screen without substantial turbulence.

Preferably, we include within the ducts deflector means as at 44, 45 and 46 relative to the ducts 33-35, respectively. Typical deflectors are seen at 44 in FIGS. 2 and 3 and include plates extending generally longitudinally of the ducts and convergent relative to each other in the direction of the fluff particle stream. Air is drawn in through openings as at 44a relative to the deflector means 44 and similar openings are provided for the deflectors 45 and 46. These deflectors 44-46 advantageously concentrate the deposition of fluff particles centrally of the width of the diaper shape which is the area most likely for receipt for excreta of infants and incontinent adults.

Operation

In the operation of the invention, the pulp webs are milled into fluff particles by the hammermills 12-14 and drawn separately through ducts 33-35 under the influence of vacuum pplied as at 23 (see FIG. 2) to a stationary plenum 22. Moving past the open ends of the ducts as at 43 relative to the duct 33 (see FIG. 1) is a screen which advantageously may be in the form of an annular drum 11. Suitable forms to shape the deposited fluff particles into hourglass shaped pads are provided as part of the screen 30.

The significant factor we have found is that turbulence is eliminated by having a gradual change in direction of the particle flow by virtue of the curvature at 33b in the leg portion of the duct and then continuing the duct into a foot-like portion overlying the annular drum 11. This results in a stratification of the fluff particles with the more concentrated or dense particles being on the outside of the curve or reverse bend so as to impinge upon the screen at a slight angle to perpendicular.

Figure 5:
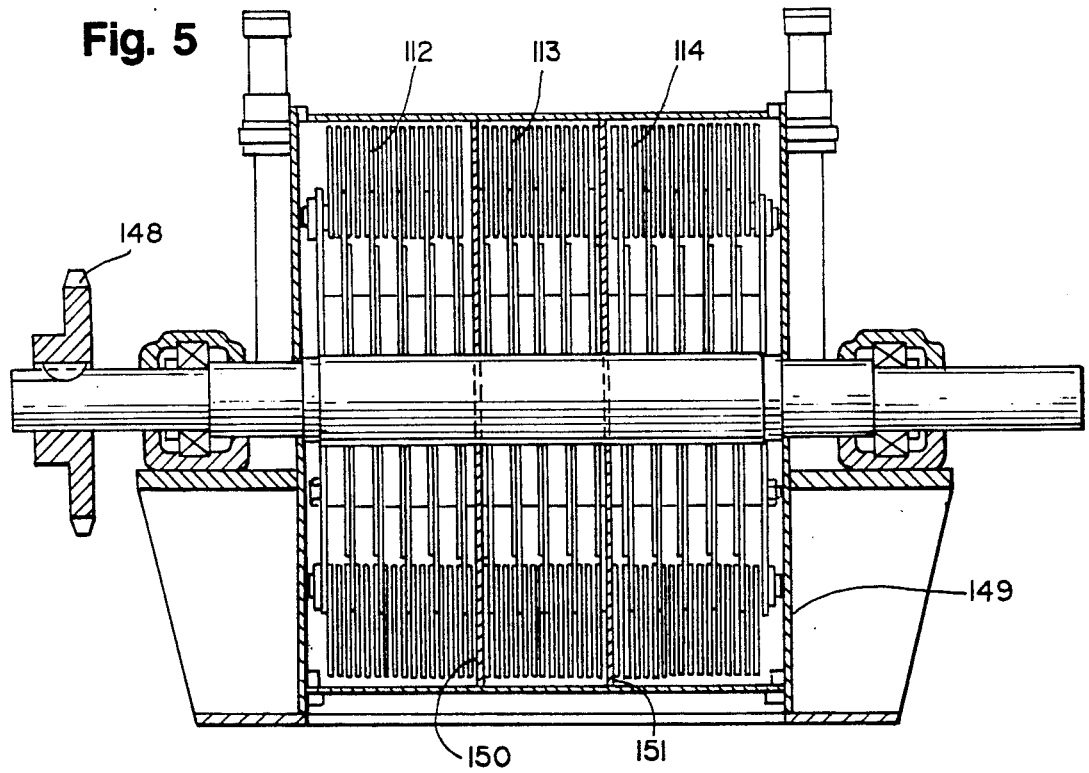
FIG. 5 is a sectional view along the line 5—5 of FIG. 4.

Embodiment of FIGS. 4-5

In some instances, particularly for space conservation, the embodiment of FIGS. 4-5 may be employed. In this embodiment, the ducts 133-5, drum 111 and takeaway conveyor 139 are substantially the same as in the FIG. 1 embodiment. What is changed is the construction of the hammermill means. As illustrated the three rotors 112, 113 and 114 are mounted on a common shaft 147 (see FIG. 5). The shaft is rotated through a drive 148 from a motor (not shown).

The housing 149 encloses the rotors 112-114 and barrier plates 150 and 151 mounted in the housing 149 maintain each rotor 112-114 in a separate chamber. As illustrated at the left hand portion of FIG. 4 three parent rolls of web material are provided, one for each chamber. For example, the web from parent roll 152 is directed to the chamber containing rotor 114, that from parent roll 153 to the chamber containing rotor 113 and the web from the parent roll 154 is delivered to the chamber containing rotor 112. The delivery is effected by pull rolls 115 mounted in the housing 149 with the three webs from the parent rolls 152-154 being arranged in side-by-side relation.

As indicated previously, the separate chambers afford the opportunity for augmenting the webs by other material, viz., recycled trim pieces, synthetic fibers, etc. The invention also contemplates employing a single parent roll with slitters to develop the three separate webs entering the housing 149.

While in the foregoing specification a detailed description of an embodiment of the invention has been set down for the purpose of illustration, many variations in the details hereingiven may be made by those skilled in the art without departing from the spirit and scope of the invention.

We claim:

1. A fluff former comprising a frame providing a longitudinally extending path, a cylindrical drum mounted in said frame having a circumferentially extending screen and an axially extending shaft, means associated with said shaft for rotating said drum one direction, a vacuum source associated with said frame for maintaining a vacuum inside said drum, fluff mill means in said path on one side of said drum to provide with said vacuum source a fluff particle stream including a plurality of separate side-by-side mill chambers, said fluff mill means including a housing equipped with spaced apart, barrier plates defining said mill chambers, a common drive shaft in said housing extending through said barrier plates and equipped with a rotor for each mill chamber, means upstream of said fluff mill means for feeding web means to each mill chamber, a takeaway conveyor in said path on the other side of said drum, a plurality of separate longitudinally extending fluff delivery ducts on said frame in said path each having a first end connected to one of said rotor mill chambers and a second end communicating with said screen, each said duct second end including a generally C-shaped section elongated in the direction of drum rotation to change the direction of flow of said stream, each said generally C-shaped section having an inner side and an outer side, each said inner side being elongated in the direction of drum rotation and each said outer side extending generally perpendicularly of said screen, each said generally C-shaped section being characterized by a radius of curvature which is at least about four times the duct height measured in the direction of the radius of curvature, whereby the outer side of each said generally C-shaped section densifies the fluff particle stream thereagainst to achieve fluff particle deposit on said screen, said drum having an axial width defining a stationary plenum, said plenum having a plurality of radial vanes defining with said screen a plurality of vacuum chambers each of which is connected to said vacuum source, each vacuum chamber extending unobstructedly across said drum axial width whereby fluff from each duct second end is deposited substantially uniformly across said axial width.

* * * * *

UNITED STATES PATENT AND TRADEMARK OFFICE
CERTIFICATE OF CORRECTION

PATENT NO. : 5,097,574
DATED : March 24, 1992
INVENTOR(S) : Hertel et al.

It is certified that error appears in the above-identified patent and that said Letters Patent is hereby corrected as shown below:

<u>Title page,</u>
Item [73], Assignee, should be -- Paper Converting Machine Company --.

Signed and Sealed this

Fifteenth Day of November, 2005

JON W. DUDAS
*Director of the United States Patent and Trademark Office*